(12) United States Patent
Nakamura et al.

(10) Patent No.: US 9,468,657 B2
(45) Date of Patent: *Oct. 18, 2016

(54) LACTIC ACID BACTERIUM AGENT FOR IMPROVING LIPID METABOLISM

(75) Inventors: Futoshi Nakamura, Kanagawa (JP); Yu Ishida, Kanagawa (JP); Shigeru Fujiwara, Kanagawa (JP)

(73) Assignee: Asahi Group Holdings, Ltd., Tokyo (JP)

( * ) Notice: Subject to any disclaimer, the term of this patent is extended or adjusted under 35 U.S.C. 154(b) by 476 days.

This patent is subject to a terminal disclaimer.

(21) Appl. No.: 13/702,742

(22) PCT Filed: Jun. 8, 2011

(86) PCT No.: PCT/JP2011/063117
§ 371 (c)(1),
(2), (4) Date: Dec. 7, 2012

(87) PCT Pub. No.: WO2011/155518
PCT Pub. Date: Dec. 15, 2011

(65) Prior Publication Data
US 2013/0089633 A1    Apr. 11, 2013

(30) Foreign Application Priority Data
Jun. 8, 2010 (JP) ................. 2010-131188

(51) Int. Cl.
| | | |
|---|---|---|
| G01N 33/554 | (2006.01) | |
| A61K 35/74 | (2015.01) | |
| A23D 7/005 | (2006.01) | |
| A23D 9/007 | (2006.01) | |
| A23L 1/30 | (2006.01) | |
| A61K 35/747 | (2015.01) | |
| A23L 2/52 | (2006.01) | |

(52) U.S. Cl.
CPC ............ *A61K 35/74* (2013.01); *A23D 7/0053* (2013.01); *A23D 7/0056* (2013.01); *A23D 9/007* (2013.01); *A23K 10/16* (2016.05); *A23L 1/3014* (2013.01); *A23L 2/52* (2013.01); *A61K 35/747* (2013.01); *A23Y 2220/00* (2013.01)

(58) Field of Classification Search
CPC .................................. A23D 7/0056
USPC .......................................... 435/7.32
See application file for complete search history.

(56) References Cited

U.S. PATENT DOCUMENTS

| | | | |
|---|---|---|---|
| 6,258,355 B1 * | 7/2001 | Cavaliere widow Vesely et al. | 424/93.45 |
| 2010/0021445 A1 | 1/2010 | Kawakami et al. | |
| 2011/0135628 A1 | 6/2011 | Sera et al. | |

FOREIGN PATENT DOCUMENTS

| | | |
|---|---|---|
| CN | 101297820 A | 11/2008 |
| CN | 101616680 A | 12/2009 |
| EP | 1995307 A1 | 11/2008 |
| JP | 04-264034 A | 9/1992 |
| JP | 2003-306436 A | 10/2003 |
| JP | 2005-225841 A | 8/2005 |
| JP | 2007-077054 A | 3/2007 |
| JP | 2007-269737 A | 10/2007 |
| JP | 2007-284360 A | 11/2007 |
| JP | 2008-156299 A | 7/2008 |
| JP | 2008-255084 A | 10/2008 |
| JP | 2009-296910 A | 12/2009 |
| WO | WO 2010/024413 A1 | 3/2010 |

OTHER PUBLICATIONS

Kouchi et al. "Location of *Streptococcus* mutants in the dentinal tubules of open infected root canals", J Dent Res., 1980, 59(12):2038-2046.*
Chassy et al. "Method for the lysis of gram-positive, asporogenous bacteria with lysozyme", Applied and Environmental Microbiology, 1980, 39(1):153-158.*
Itami et al. Aquaculture, 1998, 164:277-288.*
Di Marzio et al. J Inves Dermatol., 1999, 113:98-106.*
Wang et al. J. Chem. Tech. Biotechnol., 1996, 65:86-92.*
Machine translation of JP2007-077054, pp. 1-8.*
Machine translation of JP2003-306436, pp. 1-16.*
PCT/JP2011/063117 International Search Report completed Aug. 22, 2011.
Office Action dated Jan. 27, 2014 in CN 201180028357.5.
Supplemental European Search Report dated Nov. 15, 2013, in EP 11792475.3.
Greany et al., "Probiotic capsules do not lower plasma lipids in young women and men," European Journal of Clinical Nutrition, 2008, 62:232-237.
Hatakka et al., "*Lactobacillus rhamnosus* LC705 Together with *Propionibacterium freudenreichii* ssp *shermanii* JS Administered in Capsules in Ineffective in Lowering Serum Lipids," Journal of the American College of Nutrition, 2008, 27(4):441-447.
Lin et al., "*Lactobacillus* Effects on Cholesterol: In Vitro and in Vivo Results," J. Dairy Sci., 1989, 72:2885-2899.
Mohan et al., "Short Term Hypolipidemic Effects of Oral Lactobacillus Sporogenes Therapy in Patients with Primary Dyslipidemias," Indian Heart Journal, 1990, 42(5):361-364.
Office Action dated Apr. 21, 2016, in EP 11792475.3.

* cited by examiner

*Primary Examiner* — Bin Shen
(74) *Attorney, Agent, or Firm* — Foley & Lardner LLP

(57) ABSTRACT

This invention provides an effective means or method for improving lipid metabolism, and a means or method for treatment or prevention of diseases or disorders associated with the lipid metabolism disorder. Specifically, this invention relates to an agent for improving the lipid metabolism comprising, as active ingredients, broken cells of a lactic acid bacterium, and to a method for enhancing an effect of a lactic acid bacterium for improving the lipid metabolism comprising a step of breaking the lactic acid bacterium.

18 Claims, 9 Drawing Sheets

A

B

US 9,468,657 B2

LACTIC ACID BACTERIUM AGENT FOR IMPROVING LIPID METABOLISM

CROSS REFERENCE TO RELATED APPLICATION

This application is a national phase of International Application PCT/JP2011/063117, filed Jun. 8, 2011, which was published on Dec. 15, 2011, as WO 2011/155518 A1, which claims the benefit of Japanesse Application No. 2010-131188, filed Jun. 8, 2010. Each of the foregoing is incorporated by refrence here in its entirety.

TECHNICAL FIELD

The present invention relates to an agent (i.e., a substance) for improving lipid metabolism and, more specifically, to an agent for improving lipid metabolism comprising broken cells of a lactic acid bacterium. Further, the present invention relates to a method for producing a functional food product comprising the agent for improving lipid metabolism, a method for enhancing an effect of a lactic acid bacterium to improve lipid metabolism, a method for improving the lipid metabolism in a subject, and a pharmaceutical composition for use in treatment or prevention of diseases or disorders associated with the lipid metabolism.

BACKGROUND ART

Lactic acid bacteria or *Bifidobacteria* and their cultures (e.g., culture fluids, culture supernatants, and concentrates thereof) have been reported to be effective on improvement of the lipid metabolism, such as reduction of blood-cholesterol levels and reduction of body fat or visceral fat (e.g., Patent Literatures 1 to 6). A lot of research results have been reported on the effect of improving the lipid metabolism in humans by intake of a lactic acid bacterium. However, all such researches have yielded different results, and there is no common understanding thereamong. For example, the amount of a lactic acid bacterium to be taken is often large, and effectiveness is often evaluated with insufficiency in terms of placebo controls, double-blind experiment, and calorie control, in many literatures that demonstrate the effectiveness of intake of a lactic acid bacterium on humans (e.g., Non-Patent Literature 1). In addition, there are many reports demonstrating that intake of a lactic acid bacterium does not improve the lipid metabolism in humans (e.g., Non-Patent Literatures 2 to 4). Based thereon, the effect of improving the lipid metabolism by lactic acid bacteria is speculated to be very low.

Since lactic acid bacteria are fermentation microorganisms, in general, the live bacteria are considered to be effective, and they are often used as probiotics. Meanwhile, a treated product of a lactic acid bacterium comprising, as an active ingredient, an organic-solvent extract of the lactic acid bacterium was developed for the purpose of providing a substance having a more potent effect of improving the lipid metabolism (Patent Literature 1), although the effect thereof is limited and unsatisfactory (see Example 5 below).

In recent years, lifestyle-related diseases and metabolic syndromes are increasing due to change of eating habits and lack of physical activities. The lifestyle-related diseases and metabolic syndromes are associated with lipid metabolism abnormalities or sugar metabolism abnormalities, which often lead to the development of symptoms or diseases such as arteriosclerosis, fatty liver, hyperlipidemia, obesity, hypertension, or diabetes. When the lipid metabolism or sugar metabolism is abnormal, also, levels of lipid metabolism markers, such as cholesterol, neutral fat, and visceral fat, are known to become elevated. As such, effective means for improving the lipid metabolism are still needed in order to prevent or treat such lifestyle-related diseases and metabolic syndromes.

PRIOR ART LITERATURES

Patent Literatures

Patent Literature 1: JP Patent Publication (Kokai) No. 2007-284360 A
Patent Literature 2: JP Patent Publication (Kokai) No. 2008-24680 A
Patent Literature 3: JP Patent No. 4336992
Patent Literature 4: JP Patent Publication (Kokai) No. 2003-306436 A
Patent Literature 5: JP Patent No. 3777296
Patent Literature 6: JP Patent Publication (Kokoku) No. H06-96537 B (1994)

Non-Patent Literatures

Non-Patent Literature 1: Indian Heart J. 42 (5): 361-364, 1990
Non-Patent Literature 2: J. Dairy Sci. 72 (11): 2885-2899, 1989
Non-Patent Literature 3: Eur. J. Clin. Nutr. 62 (2): 232-237, 2008
Non-Patent Literature 4: J. Am. Coll. Nutr. 27 (4): 441-447, 2008

SUMMARY OF THE INVENTION

Problems to be Solved by the Invention

It is an object of the present invention to provide an effective means or method for improving the lipid metabolism. It is another object of the present invention to provide a means or method for treating or preventing diseases or disorders associated with the lipid metabolism abnormalities.

Means for Solving the Problems

The present inventors have extensively conducted studies in order to solve the above problems. As a result, the present inventors have now incidentally found that the effect or effect of improving the metabolism of lipids was expressed or enhanced by breaking down a lactic acid bacterium. By the effect of improving the lipid metabolism, the levels of total cholesterol, LDL-cholesterol, neutral fat, arteriosclerosis index, and visceral fat were lowered, while the levels of HDL-cholesterol and adiponectin were elevated. Such effect was superior to that of an intact lactic acid bacterium or that of organic-solvent extract of the lactic acid bacterium. The present inventors have now conceived of the use of broken cells of a lactic acid bacterium as an agent for improving the lipid metabolism based on the above finding, thereby completing the present invention.

Accordingly, the present invention is as follows.

[1] An agent for improving lipid metabolism comprising, as an active ingredient, broken cells of a lactic acid bacterium.

[2] The agent for improving lipid metabolism according to [1], wherein the lactic acid bacterium is at least one type of bacterium belonging to a genus selected from the group consisting of the genera *Lactobacillus, Bifidobacterium, Enterococcus, Leuconostoc, Streptococcus, Lactococcus, Pediococcus,* and *Weissella.*

[3] The agent for improving lipid metabolism according to [2], wherein the bacterium belonging to the genus *Lactobacillus* is at least one bacterium selected from the group consisting of the genera *Lactobacillus amylovorus, Lactobacillus gasseri, Lactobacillus casei, Lactobacillus paracasei, Lactobacillus zeae, Lactobacillus rhamnosus, Lactobacillus reuteri, Lactobacillus acidophilus, Lactobacillus crispatus, Lactobacillus gallinarum, Lactobacillus brevis, Lactobacillus fermentum, Lactobacillus plantarum, Lactobacillus delbrueckii* subsp. *bulgaricus,* and *Lactobacillus johnsonii.*

[4] The agent for improving lipid metabolism according to [2] or [3], wherein the bacterium belonging to the genus *Lactobacillus* is at least one bacterium selected from the group consisting of *Lactobacillus amylovorus* strain CP1563, *Lactobacillus amylovorus* strain CP1562, and *Lactobacillus gasseri* strain CP3238.

[5] The agent for improving lipid metabolism according to [2], wherein the bacterium belonging to the genus *Bifidobacterium* is at least one bacterium selected from the group consisting of *Bifidobacterium breve, Bifidobacterium longum, Bifidobacterium pseudolongum, Bifidobacterium animalis, Bifidobacterium adolescentis, Bifidobacterium bifidum, Bifidobacterium lactis, Bifidobacterium catenulatum, Bifidobacterium pseudocatenulatum,* and *Bifidobacterium magnum.*

[6] The agent for improving lipid metabolism according to [2], wherein the bacterium belonging to the genus *Enterococcus* is at least one bacterium selected from the group consisting of *Enterococcus faecalis, Enterococcus hirae,* and *Enterococcus faecium.*

[7] The agent for improving lipid metabolism according to [2], wherein the bacterium belonging to the genus *Streptococcus* is *Streptococcus thermophilus.*

[8] The agent for improving lipid metabolism according to [2], wherein the bacterium belonging to the genus *Leuconostoc* is at least one bacterium selected from the group consisting of *Leuconostoc mesenteroides* and *Leuconostoc lactis.*

[9] The agent for improving lipid metabolism according to [2], wherein the bacterium belonging to the genus *Lactococcus* is at least one bacterium selected from the group consisting of *Lactococcus lactis, Lactococcus plantarum,* and *Lactococcus raffinolactis.*

[10] The agent for improving lipid metabolism according to [2], wherein the bacterium belonging to the genus *Pediococcus* is at least one bacterium selected from the group consisting of *Pediococcus pentosaceus* and *Pediococcus damnosus.*

[11] The agent for improving lipid metabolism according to [2], wherein the bacterium belonging to the genus *Weissella* is at least one bacterium selected from the group consisting of *Weissella cibaria, Weissella confusa, Weissella halotolerans, Weissella hellenica, Weissella kandleri, Weissella kimchii, Weissella koreensis, Weissella minor, Weissella paramesenteroides, Weissella soli, Weissella thailandensis,* and *Weissella viridescens.*

[12] The agent for improving lipid metabolism according to any of [1] to [11], wherein the average long diameter of a broken cell of the bacterium is 0% to 90% of that of before breaking.

[13] The agent for improving lipid metabolism according to any of [1] to [12], wherein the average long diameter of a broken cell of the bacterium is 0 to 2.5 μm.

[14] The agent for improving lipid metabolism according to any of [1] to [13], wherein the broken cells of the bacterium are obtained via physical breaking.

[15] The agent for improving lipid metabolism according to any of [1] to [13], wherein the broken cells of the bacterium are obtained via chemical treatment.

[16] The agent for improving lipid metabolism according to any of [1] to [13], wherein the broken cells of the bacterium are obtained via enzymatic lysis treatment.

[17] The agent for improving lipid metabolism according to any of [1] to [13], wherein the broken cells of the bacterium are obtained via autolysis treatment.

[18] The agent for improving lipid metabolism according to any of [1] to [17], which is administered orally.

[19] The agent for improving lipid metabolism according to any of [1] to [18], which has an effect of lowering the level of at least one of total cholesterol, LDL-cholesterol, neutral fat, arteriosclerosis index, and visceral fat.

[20] The agent for improving lipid metabolism according to any of [1] to [19], which has an effect of elevating the level of at least one of HDL-cholesterol and adiponectin.

[21] The agent for improving lipid metabolism according to any of [1] to [20], which is for use in a food or drink product, feed, or medicament.

[22] The agent for improving lipid metabolism according to any of [1] to [21], which is for use in prevention or treatment of arteriosclerosis, hyperlipidemia, fatty liver, obesity, metabolic syndrome, diabetes, myocardial infarct, or cerebral infarction.

[23] A food or drink, feed, or medicament to which the agent for improving lipid metabolism according to any of [1] to [22] has been added.

[24] A method for producing a functional food or drink product, which comprises the steps of: preparing the agent for improving lipid metabolism according to any of [1] to [22]; and formulating the agent for improving lipid metabolism into a food or drink.

[25] A method for enhancing an effect of a lactic acid bacterium for improving lipid metabolism, characterized by comprising a step of breaking the lactic acid bacterium.

[26] A method for improving lipid metabolism in a subject, comprising administering broken cells of a lactic acid bacterium to the subject.

[27] A pharmaceutical composition for treatment or prevention of a disease or disorder associated with the lipid metabolism, comprising broken cells of a lactic acid bacterium and a pharmaceutically acceptable carrier.

[28] A method for producing an agent for improving lipid metabolism comprising the steps of: breaking a lactic acid bacterium; measuring an effect of the obtained broken cells of the bacterium for improving the lipid metabolism, and formulating the broken cells of the bacterium having an effect of improving the lipid metabolism into a dosage form comprising them.

[29] The *Lactobacillus amylovorus* strain CP1563, the *Lactobacillus amylovorus* strain CP 1562, or a mutant thereof.

[30] The mutant according to [29], the broken cell of which has an effect of improving lipid metabolism.

Advantage of the Invention

The present invention provides an agent for improving the lipid metabolism. The agent for improving the lipid metabolism of the present invention lowers the levels of total cholesterol, LDL-cholesterol, neutral fat, arteriosclerosis index, and/or visceral fat, and/or elevates the levels of HDL-cholesterol and/or adiponectin, thereby normalizing the lipid metabolism. Thus, such agent can be used for prevention or treatment of various diseases or disorders.

MODES FOR CARRYING OUT THE INVENTION

Figure 1:
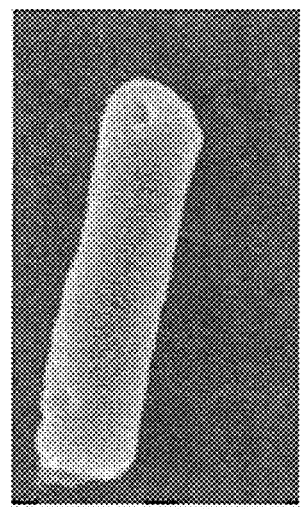
FIG. 1 shows the electron micrographs of a lactic acid bacterium before disruption treatment (A) and after disruption treatment (B).
Figure 1:
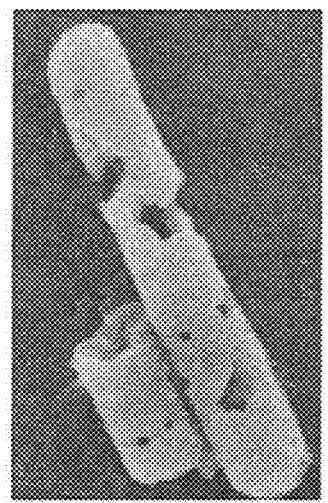

Hereafter, the present invention is described in detail. This application claims priority from Japanese Patent Application No. 2010-131188 filed on Jun. 8, 2010, and includes all or part of the contents as disclosed in the description and/or drawings thereof.

The present invention is based on the finding that the effect of a lactic acid bacterium for improving the lipid metabolism can be expressed or enhanced by breaking lactic acid bacterial cells. As such, the present invention relates to an agent for improving the lipid metabolism comprising broken cells (or a broken product) of a lactic acid bacterium, and to use of the same for medicaments and foods.

The lactic acid bacteria used in the present invention are capable of producing lactic acid from saccharides by fermentation. Examples thereof include bacteria belonging to the genera *Lactobacillus, Leuconostoc, Lactococcus, Pediococcus, Enterococcus, Bifidobacterium, Streptococcus*, and *Weissella*. According to the present invention, lactic acid bacterial cells known in the art can be used, as long as broken cells of lactic acid bacteria exhibits an effect of improving the lipid metabolism. In addition, bacterial strains that have been confirmed to be safe for animals are preferable in terms of administration to or intake by animals.

Specific examples of lactic acid bacteria include bacteria belonging to the genus *Lactobacillus*, such as *Lactobacillus amylovorus, Lactobacillus gasseri, Lactobacillus casei, Lactobacillus paracasei, Lactobacillus zeae, Lactobacillus rhamnosus, Lactobacillus reuteri, Lactobacillus acidophilus, Lactobacillus crispatus, Lactobacillus gallinarum, Lactobacillus brevis, Lactobacillus fermentum, Lactobacillus plantarum, Lactobacillus delbrueckii* subsp. *bulgaricus*, and *Lactobacillus johnsonii*.

Other specific examples of lactic acid bacteria include bacteria belonging to the genus *Bifidobacterium*, such as *Bifidobacterium breve, Bifidobacterium longum, Bifidobacterium pseudolongum, Bifidobacterium animalis, Bifidobacterium adolescentis, Bifidobacterium bifidum, Bifidobacterium lactis, Bifidobacterium catenulatum, Bifidobacterium pseudocatenulatum*, and *Bifidobacterium magnum*. Examples of bacteria belonging to the genus *Enterococcus* include *Enterococcus faecalis, Enterococcus hirae*, and *Enterococcus faecium*. An example of bacteria belonging to the genus *Streptococcus* is *Streptococcus thermophilus*. Examples of bacteria belonging to the genus *Leuconostoc* include *Leuconostoc mesenteroides* and *Leuconostoc lactis*. Examples of bacteria belonging to the genus *Lactococcus* include *Lactococcus lactis, Lactococcus plantarum*, and *Lactococcus raffinolactis*. Examples of bacteria belonging to the genus *Pediococcus* include *Pediococcus pentosaceus* and *Pediococcus damnosus*. Examples of bacteria belonging to the genus *Weissella* include *Weissella cibaria, Weissella confusa, Weissella halotolerans, Weissella hellenica, Weissella kandleri, Weissella kimchii, Weissella koreensis, Weissella minor, Weissella paramesenteroides, Weissella soli, Weissella thailandensis*, and *Weissella viridescens*.

The term "effect of improving the lipid metabolism" as used herein refers to an effect or activity of normalizing the lipid metabolism or improving the lipid metabolism disorders. Specifically, this term refers to an effect or activity of reducing the blood fat, an effect or activity of accelerating the subcutaneous fat and/or visceral fat metabolism, an effect or activity of suppressing body weight increase, and an effect or activity of normalizing fat tissue functions. Effect of improving the lipid metabolism can be evaluated by measuring blood fat levels (e.g., total cholesterol, HDL-cholesterol, LDL-cholesterol, neutral fat, and triglycerides), fat amounts (e.g., visceral fat and subcutaneous fat), body weight, and fat tissue functions (e.g., adiponectin). For example, the level of at least one of total cholesterol, LDL-cholesterol, neutral fat, arteriosclerosis index, visceral fat, and body weight is lowered by the effect of improving the lipid metabolism. In addition, the effect of improving the lipid metabolism also elevates either the level of HDL-cholesterol or the level of adiponectin. Such indicators are well-known in the art and can be measured by conventional methods or means.

Whether or not certain broken cells of a lactic acid bacterium have an effect of improving the lipid metabolism can be determined by preparing broken cells of a lactic acid bacterium, administering the obtained broken cells to subjects, such as experimental animals (e.g., animal models of obesity), and measuring for the above-described indicators in the subjects.

In the present invention, accordingly, any lactic acid bacterium can be used, as long as broken cells thereof are evaluated to have an effect of improving the lipid metabolism by the method described above. Examples of preferable lactic acid bacteria having an effect of improving the lipid metabolism include *Lactobacillus amylovorus* strain CP1563 (FERM BP-11255), *Lactobacillus amylovorus* strain CP1562 (FERM BP-11379), and *Lactobacillus gasseri* strain CP3238 (FERM BP-11256). The *Lactobacillus amylovorus* strain CP1563 and the *Lactobacillus amylovorus* strain CP1562 are lactic acid bacteria derived from the human bowel. The *Lactobacillus gasseri* strain CP3238 is a lactic acid bacterium isolated from commercially available yogurt. The broken cells of these bacterial strains were confirmed to have an effect of improving the lipid metabolism in Examples below and are available from the International Patent Organism Depositary, the National Institute of Advanced Industrial Science and Technology (AIST) (Tsukuba Central 6, 1-1-1 Higashi, Tsukuba, Ibaraki, 305-8566, Japan).

In the case of lactic acid bacteria that have already been reported to have an effect of improving the lipid metabolism, the broken cells thereof are expected to use it to enhance an effect of improving the lipid metabolism.

In the present invention, variants of the specific strains mentioned above can also be used, as long as they have an effect of improving the lipid metabolism. For example, variants of the *Lactobacillus amylovorus* strain CP1563, the *Lactobacillus amylovorus* strain CP1562, and the *Lactobacillus gasseri* strain CP3238 are highly likely to have an effect of improving the lipid metabolism, and such variants are also fallen within the scope of the present invention.

The term "variant" as used herein refers to any strain obtained from a parent strain. Specifically, this term refers to a strain obtained by a method of artificially increasing the frequency of mutation from a parent strain by means of natural mutation or mutagenesis with chemical or physical mutagens, or to a strain obtained by a specific mutagenesis technique (e.g., gene recombination). Microorganism individuals resulting from such techniques are repeatedly subjected to selection and separation, and variants with properties of interest can be obtained by microbial breeding for useful microorganisms.

For example, variants originating from *Lactobacillus amylovorus* strain CP1563, *Lactobacillus amylovorus* strain CP1562, or *Lactobacillus gasseri* strain CP3238 can be easily distinguished from other lactic acid bacterial strains based on the molecular weight distribution of amplified genomic DNA fragments of lactic acid bacteria determined by polymerase chain reaction (PCR). In short, DNA samples of lactic acid bacteria of interest are prepared, gene amplification is carried out by PCR using primers having characteristic sequence (e.g., 16S rDNA-derived nucleotide sequence), and electrophoresis patterns of the obtained fragments are analyzed. Thus, whether or not the lactic acid bacterial strain of interest is a variant originating from the *Lactobacillus amylovorus* strain CP1563, *Lactobacillus amylovorus* strain CP1562, or *Lactobacillus gasseri* strain CP3238 can be determined. It should be noted that the technique of confirming whether the bacterial strain of interest is a variant is not limited to the above, and also, whether the bacterial strain of interest is a variant can be confirmed by using techniques known in the art based on, for example, mycological properties.

By determining whether or not broken cells of the so-obtained variants have an effect of improving the lipid metabolism, lactic acid bacterial strains of interest that can be used as broken bacterial cells in the present invention can be obtained.

Lactic acid bacteria can be prepared via culture under adequate conditions using any of media ordinarily used for culture of the lactic acid bacteria. In this case, a natural or synthetic medium can be used, as long as it contains carbon source, nitrogen source, mineral salts, and the like, and a lactic acid bacterium can be cultured efficiently therein. A person skilled in the art can adequately select a known medium suitable for a bacterial strain to be used. Examples of the carbon source that can be used include lactose, glucose, sucrose, fructose, galactose, and blackstrap molasses. Examples of the nitrogen source that can be used include organic nitrogen-containing substances such as casein hydrolysate, whey protein hydrolysate, and soy protein hydrolysate. In addition, examples of the mineral salts that can be used include phosphate, sodium, potassium, and magnesium. Examples of media suitable for culture of lactic acid bacteria include MRS liquid medium, GAM medium, BL medium, Briggs Liver Broth, animal milk, skim milk, and milk-derived whey. Preferably, sterilized MRS medium can be used. Examples of natural media that can be used include tomato juice, carrot juice, other vegetable juices, apple juice, pineapple juice, and grape juice.

In addition, culturing a lactic acid bacterium can be performed at a temperature of 20° C. to 50° C., preferably 25° C. to 42° C., and more preferably approximately 37° C. under anaerobic conditions. Temperature conditions can be adjusted using a thermostatic bath, an incubator, a jacket, or the like. The term "anaerobic conditions" as used herein refers to a low-oxygen environment in which a lactic acid bacterium can proliferate. For example, anaerobic conditions can be provided by using an anaerobic chamber, anaerobic box, or airtight container or bag containing a deoxidizer, or by simply sealing a culture container. Examples of culture formats include static culture, shake culture, and tank culture. The period of culture can be 3 hours to 96 hours. It is preferable to maintain the pH of a medium in the beginning of culture at 4.0 to 8.0.

Specific examples of lactic acid bacteria preparation is briefly described below. When *Lactobacillus amylovorus* strain CP1563, *Lactobacillus amylovorus* strain CP1562, or *Lactobacillus gasseri* strain CP3238 is used, for example, the lactic acid bacterium is inoculated to a food-grade medium for culture of lactic acid bacteria, and culture is carried out overnight (for approximately 18 hours) at approximately 37° C.

After culture, the obtained culture of a lactic acid bacterium may be directly used, or if needed, the obtained culture may be further subjected to, for example, crude purification using centrifugation and/or solid-liquid separation using filtration, and to sterlization. Preferably, the lactic acid bacterial cells alone are collected via centrifugation. Lactic acid bacteria used in the present invention may be in the form of either wet cells or dried cells.

In the present invention, broken cells of lactic acid bacteria are used. As used herein, the term "broken cells" includes bacterial cells treated by means of disruption, grinding or milling, enzyme treatment, chemical treatment, or lysis. Tthe "broken cells" may also include water-soluble fractions, organic solvent-soluble fractions, fractions hardly soluble in organic solvent or in water, or fractions insoluble in organic solvent or in water, which are obtained after the cells were damaged.

The bacterial cells can be damaged by using methods and apparatuses known in the art, and examples of damaging can include physical disruption, enzymatic lysis treatment, chemical treatment, and autolysis treatment. Physical disruption may be carried out by using either a wet system (which is a treatment conducted in the state of a cell suspension) or a dry system (which is a treatment carried out in the state of a cell powder). The physical disruption may be carried out by agitation using, for example, homogenizer, ball mill, bead mill, Dyno-Mill, or satellite mill, or by pressure application using, for example, jet mill, French press, or cell disruptor, or by filtration using a filter.

Enzymatic lysis treatment can be performed to break the cell structure of a lactic acid bacterium using an enzyme, such as lysozyme.

Chemical treatment can be performed to break the cell structure of a lactic acid bacterium using a surfactant, such as glycerin fatty acid ester or soybean phospholipid.

Autolysis treatment can be performed through lysis of cells with part of enzymes possessed by a lactic acid bacterium.

In the present invention, physical disruption is preferable because the addition of other reagents or components is not needed.

When physical disruption is carried out by agitation, for example, a cell suspension or cell powder is agitated at 50 to 10,000 rpm, and preferably 100 to 1,000 rpm.

Specifically, the bacterial cells are disrupted by, for example, treating a suspension of a lactic acid bacterium in a known Dyno-Mill cell disruptor (e.g., Dyno-Mill disruptor) using glass beads at a peripheral speed of 10.0 to 20.0 m/s (e.g., about 14.0 m/s) and a treating flow rate of 0.1 to 10 L/10 min (e.g., about 1 L/10 min) at a disruption tank temperature of 10° C. to 30° C. (e.g., about 15° C.) 1 to 7 times (e.g., 3 to 5 times). Alternatively, a suspension of a lactic acid bacterium may be treated using a known wet-type jet-mill cell disruptor (e.g., JN20 Nano Jet Pul) at a discharge pressure of 50 to 1000 Mpa (e.g., 270 Mpa) at a treating flow rate of 50 to 1000 ml/min (e.g., 300 ml/min) 1 to 30 times (e.g., 10 times). Thus, the bacterial cells are disrupted. Further, lactic acid bacterial cell powder may be treated using a known dry-type satellite mill cell disruptor (e.g., GOT5 Galaxy 5) in the presence of any of different balls (e.g., 10-mm zirconia balls, 5-mm zirconia balls, or 1-mm alumina balls) at 50 to 10,000 rpm (e.g., 240 rpm or 190 rpm) for 30 minutes to 20 hours (e.g., 5 hours), thereby being able to disrupt the bacterial cells. Lactic acid bacterial cell powder may also be treated using a known wet-type jet-mill cell disruptor (e.g., Jet-O-Mizer) at a feeding speed of 0.01 to 10000 g/min (e.g., 0.5 g/min) and a discharge pressure of 1 to 1,000 kg/cm$^2$ (e.g., 6 kg/cm$^2$) 1 to 10 times (e.g., once), thereby disrupting the bacterial cells.

According to the present invention, although the broken cells of a lactic acid bacterium exert the above-described effect even when the cells are merely perforated, it is preferable to prepare the broken cells so that the average long diameter of the cell of a lactic acid bacterium is 90% or less of that of before breaking treatment. When cells are broken via lysis treatment, for example, the average long diameter of the cells may occasionally be 0%. As such, the lactic acid bacterium may be broken so that the average long diameter of broken cell products is 0% to 90%, preferably 0% to 80%, more preferably 0% to 70%, further preferably 0% to 50%, and still further preferably 0% to 20% of that of before breaking.

The average long diameter of the broken cells of a lactic acid bacterium varies depending on the type of the lactic acid bacterium to be used. For example, it is 0 to 2.5 µm, preferably 0 to 2 µm, more preferably 0 to 1.5 µm, further preferably 0 to 1 µm, and still further preferably 0 to 0.5 µm.

Specifically, the average long diameter is measured by the method described in Example 1.

Desirably, intact cells and/or broken cells of a lactic acid bacterium may be subjected to a further treatment. Examples of such treatment are described below.

Intact cells and/or broken cells of a lactic acid bacterium can be prepared in the form of a suspension or diluted solution by suspending or diluting the cells in an adequate solvent. Examples of a solvent that can be used include water, physiological saline, and phosphate buffered saline (PBS).

The intact cells and/or broken cells of a lactic acid bacterium can be treated by sterilization to prepare a sterilized product. The sterilization of such intact cells and/or broken cells can be performed by a conventional technique, such as filtration sterilization, radiation sterilization, heat sterilization, or pressure sterilization.

Alternatively, the intact cells and/or broken cells of a lactic acid bacterium can be treated by heating to prepare a heated product. To obtain such heated product, the treatment of intact cells and/or broken cells of a lactic acid bacterium at an elevated temperature (e.g., at 80° C. to 150° C.) is performed for a predetermined period of time, for example, about 10 minutes to 1 hour (e.g., about 10 to 20 minutes).

Further, the intact cells and/or broken cells of a lactic acid bacterium can be processed into the form of powder or granules via drying. Examples of drying methods include, but are not particularly limited to, spray dry, drum dry, vacuum dry, and lyophilization, which can be used alone or in combination. Upon drying, excipients that are conventionally used may be optionally added.

Further, an ingredient or fraction having an effect of improving the lipid metabolism may be purified from the intact cells and/or broken cells of a lactic acid bacterium by a known separation or purification method. Examples of such method include: a method utilizing solubility, such as salt precipitation or organic solvent precipitation; a method utilizing a difference in molecular weight, such as dialysis, ultrafiltration, or gel filtration; a method utilizing a difference in charge, such as ion-exchange chromatography; a method utilizing specific affinity, such as affinity chromatography; and a method utilizing hydrophobicity, such as hydrophobic chromatography. These methods can be used alone or in combinations of two or more methods.

The treatments described above may be carried out alone or, if needed, in combination. According to the present invention, such treated product can be used as an agent for improving the lipid metabolism.

Through continuous intakes of the broken cells of a lactic acid bacterium obtained above, alone or in combination with other ingredients, as an agent for improving the lipid metabolism, the effect of improving the lipid metabolism, resulting in a therapeutic or preventive effect of diseases or disorders associated with the lipid metabolism, can be expected. Also, the agent for improving the lipid metabolism can be added to drinks (or beverage), foods, or feeds.

The agent for improving the lipid metabolism of the present invention comprises, as an active ingredient, the broken cells of a lactic acid bacterium as described above. Such agent may comprise broken cells of a single lactic acid bacterium, broken cells of a plurality of different lactic acid bacteria, or combined broken cells of a lactic acid bacterium or lactic acid bacteria subjected to different breaking treatments.

In addition to the broken cells of lactic acid bacteria used as active ingredients, below-mentioned additives or other known lipid metabolism improving agents may further be added to the agent for improving the lipid metabolism of the present invention, alone or in combination, with the proviso that the desired effect is not inhibited.

The dosage form of the agent for improving the lipid metabolism of the present invention is not particularly limited. Examples of dosage forms include: oral formulations, such as tablets, capsules, granules, powders, dust formulations, syrups, dry syrups, liquids, suspensions, and inhalers; enteral formulations such as suppositories; infusions; and injections. Among them, an oral formulation is preferred. In case of a liquid formulation, such as liquid or suspension, it may be dissolved or suspended in water or a different adequate medium immediately before use. When the agent for improving the lipid metabolism of the present invention is formulated into the form of a tablet or granules, a surface coating may be provided by a well-known method. Further, the agent for improving the lipid metabolism of the present invention may be prepared into the dosage form of a controlled-release formulation such as sustained-release formulation, delayed-release formulation, or an immediate release formulation with the use of techniques known in the art.

The agent for improving the lipid metabolism, which is in a dosage form as described above, can be produced, using conventional methods, by formulating generally used additives, such as excipients, disintegrators, binders, wetting agents, stabilizers, buffers, lubricants, preservatives, surfactants, sweeteners, corrigents, aromatics, acidulants, and coloring agents, into the ingredients as described above, depending on types of dosage forms. Where the agent for improving the lipid metabolism is prepared into a pharmaceutical composition, for example, pharmaceutically acceptable carriers or additives can be formulated into the agent for improving the lipid metabolism of the present invention. Examples of the pharmaceutically acceptable carriers and additives include water, pharmaceutically acceptable organic solvents, collagen, polyvinyl alcohol, polyvinyl pyrrolidone, carboxyvinyl polymers, sodium alginate, water-soluble dextran, water-soluble dextrin, sodium carboxymethyl starch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, lactose, surfactants acceptable as pharmaceutical additives, and artificial cell constructs such as liposomes.

Where the agent for improving the lipid metabolism of the present invention contains the above-described additives, other lipid metabolism improving agents, or the like, the content of the broken lactic acid bacterial cells used as active ingredients varies depending on dosage forms. The amount of lactic acid bacterial cells before breaking treatment is generally 0.0001% to 99% by mass, preferably 0.001% to 80% by mass, and more preferably 0.001% to 75% by mass. It is preferable that the agent for improving the lipid metabolism be prepared into a dosage form that allows management of the daily dose, so that a preferable amount of the active ingredient can be administered. In addition, broken lactic acid bacterial cells are contained in the agent for improving the lipid metabolism of the present invention in an amount of approximately $10^7$ cells/g to approximately $10^{12}$ cells/g, and preferably approximately $10^8$ cells/g to approximately $10^{12}$ cells/g, when counted as the number of lactic acid bacterial cells before breaking.

Examples of other lipid metabolism improving agents that can be added to or incorporated into the agent for improving the lipid metabolism of the present invention include, but are not limited to, lipid-reducing drugs (e.g., statins, fibrates, and eicosapentaenoic acid) and vitamins (e.g., nicotinic acid and vitamin E).

The agent for improving the lipid metabolism of the present invention may further contain a variety of additives used for production of medicaments, foods or drinks, feeds, and other various substances. Examples of such substances and additives include a variety of fats and oils (e.g., plant oils, such as soybean oil, corn oil, safflower oil, and olive oil, and animal fats and oils, such as beef fat and sardine oil), crude drugs (e.g., royal jelly and ginseng), amino acids (e.g., glutamine, cysteine, leucine, and arginine), polyalcohols (e.g., ethylene glycol, polyethylene glycol, propylene glycol, glycerin, and sugar alcohols such as sorbitol, erythritol, xylitol, maltitol, and mannitol), natural polymers (e.g., gum arabic, agar, water-soluble corn fibers, gelatin, xanthan gum, casein, gluten or gluten hydrolysate, lecithin, starch, and dextrin), vitamins (e.g., vitamin C and B-complex vitamins), minerals (e.g., calcium, magnesium, zinc, and iron), dietary fibers (e.g., mannan, pectin, and hemicellulose), surfactants (e.g., glycerin fatty acid esters and sorbitan fatty acid esters), purified water, excipients (e.g., glucose, cornstarch, lactose, and dextrin), stabilizers, pH-adjusting agents, antioxidants, sweeteners, taste components, acidulants, coloring agents, and flavors.

Apart from the above-described active ingredient, further, a functional ingredient(s) or an additive(s) can be incorporated into the agent for improving the lipid metabolism of the present invention. Examples thereof include taurine, glutathione, carnitine, creatine, coenzyme Q, glucuronic acid, glucuronolactone, capsicum extract, ginger extract, cacao extract, guarana extract, garcinia extract, theanine, γ-aminobutyric acid, capsaicin, capsiate, a variety of organic acids, flavonoids, polyphenols, catechins, xanthine derivatives, indigestible oligosaccharides such as fructooligosaccharides, and polyvinyl pyrrolidone.

The amount of such additive can be adequately determined depending on the type of additive and the desirable amount. The content of broken cells of a lactic acid bacterium used as active ingredient varies depending on the dosage form. The content is generally 0.0001% to 99% by mass, preferably 0.001% to 80% by mass, and more preferably 0.001% to 75% by mass, as the amount of the lactic acid bacterium before breaking.

Subjects of administration or intake of the agent for improving the lipid metabolism of the present invention are vertebrate animals. Specific examples thereof include mammals such as humans, primates (e.g., monkeys and chimpanzees), livestock animals (e.g., cattle, horses, pigs, and sheep), pet animals (e.g., dogs and cats), and experimental animals (e.g., mice and rats). Further, such subjects can be reptiles and birds. Particularly preferable subjects are humans who have already developed a lipid metabolism disorder, humans who are at a high risk of developing a lipid metabolism disorder due to genetic or environmental factors, or humans who had suffered from a lipid metabolism disorder in the past.

The dose of administration or intake of the agent for improving the lipid metabolism of the present invention varies depending on the age and body weight of a subject, the administration/intake route, the number of doses for administration/intake, the severity of the lipid metabolism disorders, and other conditions. The dose can be changed extensively at the discretion of a person skilled in the art to achieve a desired effect. For oral administration or intake, for example, it is preferable to administer broken cells of a lactic acid bacterium contained in the agent for improving the lipid metabolism in an amount of generally approximately $10^6$ cells to $10^{12}$ cells, and preferably approximately $10^7$ cells to $10^{11}$ cells per kg of body weight, as the amount of the lactic acid bacterium before breaking treatment. The content of broken cells of a lactic acid bacterium is not particularly limited and can be adequately adjusted in accordance with the ease of production, the preferable daily dose, or other conditions. Since the agent for improving the lipid metabolism of the present invention is highly safe, it is also possible to further increase the dose to be administered. A daily dose may be administered in a single dosage, or it may be administered in several separate dosages. In addition, the frequency of administration or intake is not particularly limited, and it can be adequately selected depending on various conditions, such as route of administration or intak, age or body weight of a subject, severity of lipid metabolism disorders, presence or absence of onset of a disease or disorder caused by lipid metabolism disorders, and desired effects (e.g., therapeutic or preventive effects).

The administration or intake route of the agent for improving the lipid metabolism of the present invention is not particularly limited, and it can be, for example, oral administration or intake, or parenteral administration (e.g., intrarectal, subcutaneous, intramuscular, or intravenous administration). Particularly preferably, the agent for improving the lipid metabolism of the present invention is orally administered or taken.

The agent for improving the lipid metabolism of the present invention has an effect of lowering the blood fat, an effect of accelerating the subcutaneous fat and/or visceral fat metabolism, and an effect of suppressing body weight increase of a subject. Specifically, the agent for improving the lipid metabolism of the present invention has an effect of lowering the levels of total cholesterol, LDL-cholesterol, neutral fat, arteriosclerosis index, and/or visceral fat, and/or elevating the levels of HDL-cholesterol and/or adiponectin of a subject, thereby normalizing the lipid metabolism. Thus, the agent for improving the lipid metabolism of the present invention exerts excellent preventive, ameliorative, and therapeutic effects on diseases or disorders associated with the lipid metabolism. In addition, such agent is highly safe, and it is thus easy to continuously intake such agent for a long period of time. As such, the agent for improving the lipid metabolism of the present invention can be added to foods or drinks and feeds.

As described above, the agent for improving the lipid metabolism of the present invention can be used for prevention or treatment of diseases or disorders associated with the lipid metabolism in a pharmaceutical composition, or it can be added to a functional food or drink in order to use for intended purposes. The term "diseases or disorders associated with the lipid metabolism" used herein refers to diseases, disorders, symptoms, or syndromes resulting from abnormalities in the lipid metabolism. Examples of diseases or disorders associated with the lipid metabolism include, but are not limited to, arteriosclerosis, hyperlipidemia, fatty liver, obesity, metabolic syndrome, diabetes, and circulatory system diseases (e.g., myocardial infarct and cerebral infarction).

In the present invention, the term "prevention or treatment" of diseases or disorders associated with the lipid metabolism refers to prevention of the onset of diseases or disorders associated with the lipid metabolism or treatment of the developed diseases or disorders associated with the lipid metabolism (i.e., the disease state) of a subject such as an animal or human. The term also refers to delay or suppression of the development of diseases or disorders associated with the lipid metabolism. Further, this term refers to prevention of the onset of diseases or disorders resulting from diseases or disorders associated with the lipid metabolism. When the agent for improving the lipid metabolism of the present invention is used for a preventive purpose, for example, it is preferable that the agent be administered to subjects having genetic factors, environmental factors, or other abnormalities that may cause diseases or disorders associated with the lipid metabolism, or subjects who had developed diseases or disorders associated with the lipid metabolism in the past. Such subjects may be allowed to intake the agent.

The target disease or disorder associated with the lipid metabolism to be treated or prevented with the aid of the agent for improving the lipid metabolism may be a single or combined diseases or disorders, or may be combined with a disease other than those mentioned above.

The agent for improving the lipid metabolism of the present invention may be used in combination with an other medicament or an other therapeutic or preventive method. The "other medicament" and the agent for improving the lipid metabolism of the present invention may be formulated into a single formulation. Alternatively, they may be formulated into separate formulations to administer them simultaneously or at intervals.

As described above, the agent for improving the lipid metabolism of the present invention has an effect of improving the lipid metabolism. In addition, such agent comprises lactic acid bacteria that has been conventionally used for meals and thus is highly safe. Even when it is added to a variety of foods or drinks, further, it does not inhibit the flavor of a food or drink itself. Thus, it can be added to a variety of foods or drinks and can be continuously taken. This can lead to an improvement of the lipid metabolism accordingly.

The food or drink of the present invention comprises the agent for improving the lipid metabolism as described above. In the present invention, the food or drink includes beverages. Examples of the food or drink comprising the agent for improving the lipid metabolism of the present invention include all foods or drinks into which the above agent for improving the lipid metabolism can be incorporated, in addition to foods or drinks such as health foods or drinks, functional foods or drinks, and foods or drinks for specified health use.

Functional foods or drinks are particularly preferable as foods or drinks containing the agent for improving the lipid metabolism of the present invention. The "functional food or drink" of the present invention means a food or drink having a predetermined function for organisms and encompasses, for example, all of so-called health foods or drinks such as foods or drinks with health claims including foods for specified health use (including conditional FOSHU [food for specified health use]) and foods or drinks with nutrient function claims, foods or drinks for special dietary uses, nutritional supplements, health supplements, supplements (e.g., those having a variety of dosage forms such as tablets, coated tablets, sugar-coated tablets, capsules, and liquid agents), and beauty foods or drinks (e.g., diet foods or drinks). The functional foods or drinks of the present invention also encompass health foods or drinks to which health claim based on Codex (Joint FAO/WHO Food Standards Programme) food standards are applied.

Specific examples of foods or drinks include health foods or drinks and nutritional supplements in preparation forms such as liquid diets (e.g., tube enteral nutritional supplements), tablet candies, tablets, chewable tablets, tablets, dust formulations, powders, capsules, granules, and tonic drinks; tea beverages such as green tea, oolong tea, and black tea; drinks or beverages such as soft drinks, jelly beverages, sport beverages, milk beverages, carbonated beverages, vegetable beverages, juice beverages, fermented vegetable beverages, fermented juice beverages, fermented milk beverages (e.g., yogurt), lactic acid bacteria beverages, milk beverages (e.g., coffee milk and fruit milk), beverages containing drink powders, cocoa beverages, milk, and purified water; spreads such as butter, jam, dried seasoning products, and margarine; mayonnaise; shortening; custard; dressings; breads; boiled rice; noodles; pasta; Japanese miso soup; Japanese tofu; yogurt; soups or sauces; and sweets (e.g., biscuits and cookies, chocolates, candies, cakes, ice creams, chewing gums, and tablets).

The food or drink of the present invention can be produced by conventional methods by adding other food materials used for production of the above-mentioned foods or drinks, various nutrients, various vitamins, minerals, dietary fibers, and various additives (e.g., taste components, sweeteners, acidulants such as organic acids, stabilizers, and flavors), in addition to the above-mentioned agent for improving the lipid metabolism.

For the food or drink of the present invention, a person skilled in the art can adequately determine the amount of the agent for improving the lipid metabolism formulated in consideration of the form of the food or drink and the taste or texture that are required. Usually, an appropriate amount of the agent for improving the lipid metabolism to be added is generally 0.0001% to 99% by mass, preferably 0.001% to 80% by mass, and more preferably 0.001% to 75% by mass in total of broken cells of a lactic acid bacterium in the agent for improving the lipid metabolism, as the amount of a lactic acid bacterium before breaking treatment. The agent for improving the lipid metabolism of the present invention is safe. As such, the amount of the agent in a food or drink can be further increased. In order to achieve consumption of the desirable amount of the agent for improving the lipid metabolism, it is desirable to prepare the agent for improving the lipid metabolism in a dosage form that allows management of the daily dose. As described above, the food or drink of the present invention can be consumed in a manner that allows management of a desirable amount of the agent for improving the lipid metabolism of the present invention. Accordingly, a method for preventing and improving diseases or disorders associated with the lipid metabolism using the food or drink can be provided.

The agent for improving the lipid metabolism of the present invention may be incorporated into a food or drink by an arbitrary appropriate method available to a person skilled in the art. For example, the agent for improving the lipid metabolism of the present invention can be prepared in a form of liquid, gel, solid, powder, or granules and then incorporated into foods or drinks. Alternatively, the agent for improving the lipid metabolism of the present invention may be mixed or dissolved directly into raw materials for foods or drinks. The agent for improving the lipid metabolism of the present invention may be applied to, coated onto, infiltrated into, or sprayed onto food or drinks. The agent for improving the lipid metabolism of the present invention may be dispersed uniformly or distributed unevenly in food or drinks. A capsule or the like containing the agent for improving the lipid metabolism of the present invention may be prepared. An edible film or food coating agent may be wrapped around the agent for improving the lipid metabolism of the present invention. Alternatively, the agent for improving the lipid metabolism of the present invention may be prepared into a form such as tablet after the addition of an appropriate excipient or the like. The food or drink comprising the agent for improving the lipid metabolism of the present invention may further be processed. Such a processed product also falls within the scope of the present invention.

In the production of the food or drink product of the present invention, a variety of additives routinely used in foods or drinks may be employed. Examples of the additives include, but are not limited to, color formers (e.g., sodium nitrite), coloring agents (e.g., gardenia pigments and Red 102), flavors (e.g., orange flavors), sweeteners (e.g., stevia and aspartame), preservatives (e.g., sodium acetate and sorbic acid), emulsifiers (e.g., sodium chondroitin sulfate and propylene glycol fatty acid ester), antioxidants (e.g., disodium EDTA and vitamin C), pH adjusting agents (e.g., citric acid), chemical seasonings (e.g., sodium inosinate), thickeners (e.g., xanthan gum), swelling agents (e.g., calcium carbonate), antifoaming agents (e.g., calcium phosphate), binders (e.g., sodium polyphosphate), nutrition-enriching agents (e.g., calcium-enriching agents and vitamin A), and excipients (e.g., water-soluble dextrin). Functional raw materials such as Panax ginseng extracts, *Acanthopanax senticosus Harms* extracts, eucalyptus extracts, or du zhong tea extracts may further be added.

As described above, the food or drink of the present invention has an effect of improving the lipid metabolism. As such, it exhibits an excellent effect of preventing or ameliorating diseases or disorders associated with the lipid metabolism. In addition, it is safe, and thus there is no concern about side effects. Further, the agent for improving the lipid metabolism of the present invention has a favorable flavor. Even when it is added to a variety of foods or drinks, therefore, it does not inhibit the flavor of a food or drink itself. Accordingly, the so obtained food or drink can be easily used for long-term continuous intake. Thus, the effect of preventing or improving diseases or disorders associated with the lipid metabolism will be able to be expected.

Furthermore, the agent for improving the lipid metabolism of the present invention can be formulated not only into foods or drinks for humans but also into feeds for animals such as livestock, racehorses, and pets. Feeds are substantially equivalent to foods or drinks except that they are given to non-human subjects. Therefore, the above descriptions of foods or drinks can also be applied to feeds.

The present invention will hereafter be described in greater detail with reference to the following examples, although the present invention is not limited thereto.

EXAMPLE 1

The lactic acid bacteria *Lactobacillus amylovorus* strain CP1563 (FERM BP-11255) and *Lactobacillus gasseri* strain CP3238 (FERM BP-11256) were prepared in the manner described below.

The *Lactobacillus amylovorus* strain CP1563 was sampled and isolated from human feces, and the *Lactobacillus gasseri* strain CP3238 was sampled and isolated from commercially available yogurt. The strains were identified based on 16S rDNA nucleotide sequence analysis and phenotype observation.

These strains were deposited under Accession Numbers FERM BP-11255 and FERM BP-11256 as of May 25, 2010, with the International Patent Organism Depositary, the National Institute of Advanced Industrial Science and Technology (AIST) (Tsukuba Central 6, 1-1-1 Higashi, Tsukuba, Ibaraki, 305-8566, Japan) under the terms of the Budapest Treaty for deposition of patent microorganisms.

The lactic acid bacteria were each cultured using a homemade, food-grade medium for lactic acid bacteria at 37° C. for 18 hours and then collected via centrifugation. The bacterial strains were each washed with deionized water, harvested, resuspended in an adequate amount of water, and sterilized at a temperature of 90° C. The sterilized suspension was subjected to disruption using Dyno-Mill under conditions as described below.

Apparatus used: Dyno-Mill disruptor (Multi-Lab 0.6 L, Shinmaru Enterprises Corporation)
Peripheral speed: 14.0 m/s
Treating flow rate: 1 L/10 min
Number of treatments: 5 times
Disruption tank temperature: 15° C.
Glass beads used: diameter 0.5 mm, 0.4 L As a result of disruption (breaking) treatment, the average long diameter of cells in the suspension of the lactic acid bacterium was reduced to 68% of that before treatment (i.e., 2.77 µm—>1.89 µm). The average long diameter of cells was measured in the manner described below.

Lyophilized powder of disrupted (broken) or undisrupted (unbroken) lactic acid bacterium (5 mg) was suspended in 1 mL of pure water, the suspension was ultrasonically treated using an ultrasonic apparatus (USD-5R, AS One Corporation) (output: 240 W) for 2 minutes to prepare a dispersion, and the assay sample was thus prepared. The resulting assay sample (about 10 µL) was fixed onto a sample table (S-KM, Ø15×14×6, aluminum, Nisshin EM Corporation), which had been hydrophilized using an ion sputtering apparatus (Hitachi High-Technologies Corporation), and then subjected to Pt—Pd vapor deposition using an ion sputtering apparatus. Vapor deposition treatment was carried out using an ion sputtering apparatus (E-1010, Hitachi High-Technologies Corporation) using the target Pt—Pd with a vacuum of 7 Pa at a current of 12 mA for 30 seconds. The sample was microscopically observed under a scanning electron microscope (SEM), 10 to 20 microscopic images were photographed under the conditions described below, long diameters of 100 or more cells (including granular cells) in the images were measured, and the average value thereof was designated as the average long diameter. Granules at the edge of the image were not measured. Membrane-like substances were not to be measured. Granules were subjected to measurement. The "long diameters" were measured by analyzing the photographed images using image-analyzing particle diameter distribution software. Such analysis was carried out by measuring the longer side of the short side and the long side of a circumscribed rectangle that minimizes an area circumscribed with the particles (or cells).

<Measurement Conditions>
Apparatus conditions: ACCELERATING VOLTAGE/5 kv, W. D./5.0 mm
Magnification: ×5,000
Image signal: SE (SECONDARY ELECTRON)

FIG. 1 shows a microscopic photograph of cells before disruption treatment (A) and after disruption treatment (B). As shown in FIG. 1B, completely disrupted cells (left) and perforated cells (right) were obtained by the disruption treatment. After disruption treatment, the suspension was lyophilized, and lyophilized powder of disrupted lactic acid bacterium was obtained. When the cells were not disrupted (as a control), the sterilized solution as such was lyophilized, and lyophilized powder of undisrupted lactic acid bacterium was obtained.

Comparative Example

The organic-solvent-extracted lactic acid bacterium described in Patent Literature 1 above was prepared for comparison. Patent Literature 1 describes organic-solvent-extracted lactic acid bacterium prepared by adding an organic solvent to dried cells of the lactic acid bacterium, subjecting the mixture to ultrasonic treatment, concentrating the resulting supernatant to dryness, and adding an organic solvent to the dry matter.

Ethanol (100 ml) was added to 10 g lyophilized powder of the lactic acid bacterium Lactobacillus amylovorus strain CP1563, which was then ultrasonically treated for 5 minutes and centrifuged at 7,500×g, at 4° C. for 15 minutes, and the supernatant was recovered. The obtained supernatant was concentrated to dryness using a rotary evaporator, and ethanol was added to the dry matter to obtain 1 g of an extract. This procedure was repeated, and, consequently, total 15 g of the extract was obtained.

EXAMPLE 2

In this Example, the effects of lactic acid bacteria on a dietary-induced obesity mouse model were examined.

At the outset, raw materials were mixed to produce high-fat feeds containing a lactic acid bacterium and having compositions as shown in Table 1.

TABLE 1

| | | Wt. % | | | |
|---|---|---|---|---|---|
| Raw materials | Control | Feed containing 0.25% lactic acid bacterium | Feed containing 0.5% lactic acid bacterium | Feed containing 1.0% lactic acid bacterium | Feed containing organic-solvent-extracted 0.1% lactic acid bacterium |
| Butter | 15.00 | 15.00 | 15.00 | 15.00 | 15.00 |
| Sucrose | 52.45 | 52.45 | 52.45 | 52.45 | 52.45 |
| Casein | 20.00 | 20.00 | 20.00 | 20.00 | 20.00 |
| Corn oil | 1.00 | 1.00 | 1.00 | 1.00 | 1.00 |
| Cellulose | 5.00 | 4.75 | 4.50 | 4.00 | 4.90 |
| Mineral mixture | 3.50 | 3.50 | 3.50 | 3.50 | 3.50 |
| Vitamin mixture | 1.00 | 1.00 | 1.00 | 1.00 | 1.00 |
| Choline chloride | 0.25 | 0.25 | 0.25 | 0.25 | 0.25 |
| Cystine | 0.30 | 0.30 | 0.30 | 0.30 | 0.30 |
| Cholesterol | 1.00 | 1.00 | 1.00 | 1.00 | 1.00 |
| Sodium cholate | 0.50 | 0.50 | 0.50 | 0.50 | 0.50 |
| Lyophilized powder of lactic acid bacterium | 0.00 | 0.25 | 0.50 | 1.00 | 0.00 |
| Organic-solvent-extracted lactic acid bacterium | 0.00 | 0.00 | 0.00 | 0.00 | 0.10 |

In the patent documents described in the Background Art section above, animal models of obesity were prepared using high-fat feeds comprising soybean oil or lard as a major lipid source, and the effects of lactic acid bacteria were examined. Since lactic acid bacteria have not yet demonstrated effect of improving the lipid metabolism on humans, butter was used as a major lipid source in order to prepare obesity animal models of more serious conditions. Compared with soybean oil or lard, butter contains less unsaturated fatty acid and more saturated fatty acid. If butter is used as a major lipid source, the lipid metabolism becomes poorer, and detection of the effects of lactic acid bacteria becomes more difficult. It was thus considered that the results attained under such conditions were similar to the results of evaluation made with respect to humans.

C57BL/6 male mice (5-week-old) were preliminary raised by feeding the high-fat feed prepared in the manner described above (control feeds) for 1 week to prepare an obsity mouse model. Subsequently, the prepared mouse model was raised by feeding the high-fat feeds containing various types of lactic acid bacteria for 6 weeks to 3 months. Mouse model was raised in accordance with the pair feeding method, and the amounts of feeds to be taken were adjusted to be equivalent among groups. Blood samples were obtained at the end of the experiment, and the effects of lactic acid bacteria were examined based on various types of markers in the blood.

Specifically, Experiments 1 and 2 described below were performed.

Experiment 1:
  Groups to which the control feed was administered:
  group to which the feed containing 1% undisrupted *Lactobacillus amylovorus* CP1563 was administered; and
  group to which the feed containing 1% disrupted *Lactobacillus amylovorus* CP1563 was administered.

Experiment 2:
  Groups to which the control feed was administered:
  group to which the feed containing 1% undisrupted *Lactobacillus gasseri* CP3238 was administered; and
  group to which the feed containing 1% disrupted *Lactobacillus gasseri* CP3238 was administered.

Figure 2:
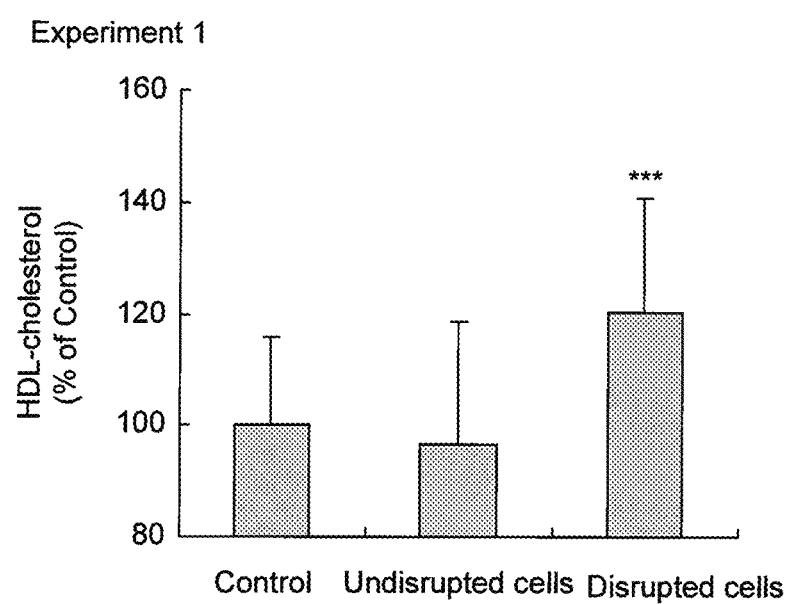
FIG. 2 is the graph showing an effect of disrupted cells of the lactic acid bacterium *Lactobacillus amylovorus* strain CP1563 on a dietary-induced obesity model (HDL-cholesterol).
Figure 3:
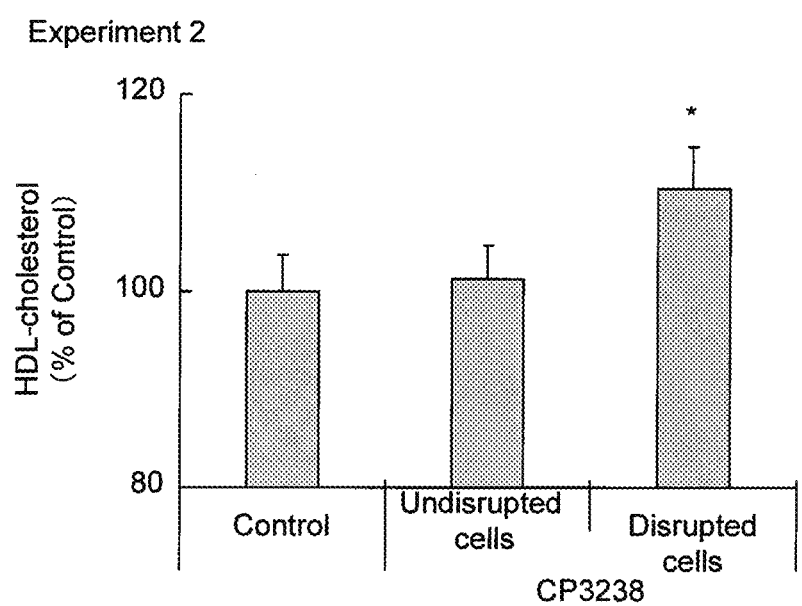
FIG. 3 is the graph showing an effect of disrupted cells of the lactic acid bacterium *Lactobacillus gasseri* strain CP3238 on a dietary-induced obesity model (HDL-cholesterol).

The results of Experiments 1 and 2 are shown in FIG. 2 and FIG. 3, respectively. As shown in FIG. 2 and FIG. 3, no changes were observed in the HDL-cholesterol level in the groups to which feeds containing undisrupted lactic acid bacteria CP1563 and CP3238 had been administered, compared with the control group. In the groups to which feeds containing disrupted lactic acid bacteria CP1563 and CP3238 had been administered, the HDL-cholesterol level was significantly improved ($p<0.001$, $p=0.037$). This demonstrates that the effect of improving the lipid metabolism can be remarkably enhanced by disrupting lactic acid bacteria.

EXAMPLE 3

In this Example, dose-dependency of the effect of a lactic acid bacterium on the dietary-induced obesity mouse model was examined.

Specifically, the mouse model of obesity described in Example 2 was raised by feeding high-fat feeds containing disrupted *Lactobacillus amylovorus* CP1563 (lactic acid bacterium content: 0%, 0.25%, 0.5%, 1.0%). Thereafter, the levels of HDL-cholesterol and arteriosclerosis index of the obesity mouse model were measured. The arteriosclerosis index was determined by the following equation:

$$\text{arteriosclerosis index} = (\text{total cholesterol} - \text{HDL cholesterol}) / \text{HDL cholesterol}.$$

Figure 4:
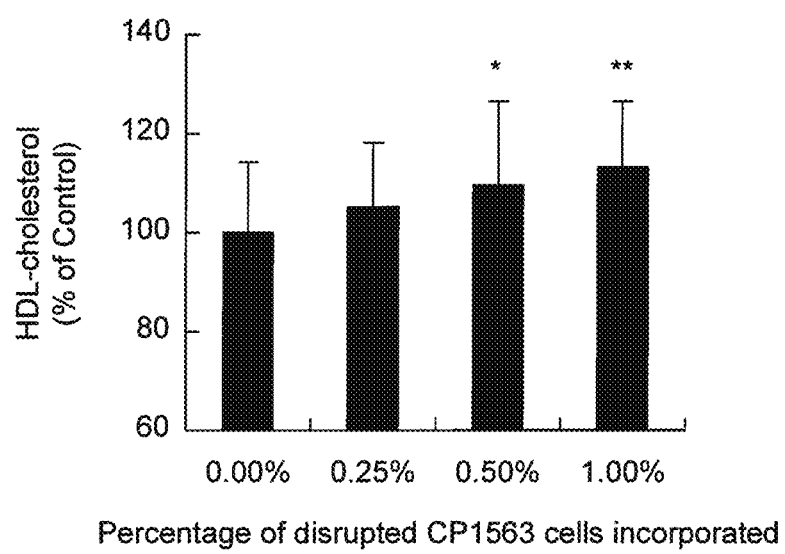
FIG. 4 is the graph showing a dose-dependent effect of disrupted cells of a lactic acid bacterium on a dietary-induced obesity model (HDL-cholesterol).
Figure 5:
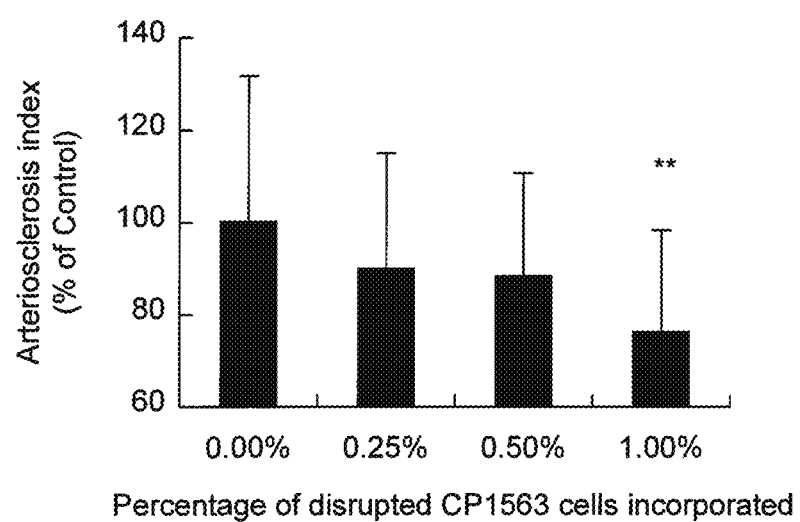
FIG. 5 is the graph showing a dose-dependent effect of disrupted cells of a lactic acid bacterium on a dietary-induced obesity model (arteriosclerosis index).

The results are shown in FIG. 4 (HDL-cholesterol) and in FIG. 5 (arteriosclerosis index). As a result of administration of disrupted cells of the strain CP1563, the levels of HDL-cholesterol and arteriosclerosis index were improved in a dose-dependent manner.

EXAMPLE 4

In this Example, anti-metabolic-syndrome effect of a lactic acid bacterium on the dietary-induced obesity mouse model was examined.

Specifically, the obesity mouse model described in Example 2 was raised by feeding high-fat feeds containing disrupted *Lactobacillus amylovorus* CP1563 (lactic acid bacterium content: 0%, 1%). Thereafter, the levels of HDL-cholesterol, LDL-cholesterol, neutral fat, arteriosclerosis index, polymeric adiponectin, and visceral fat weight of the obesity mouse model y were measured.

Figure 6:
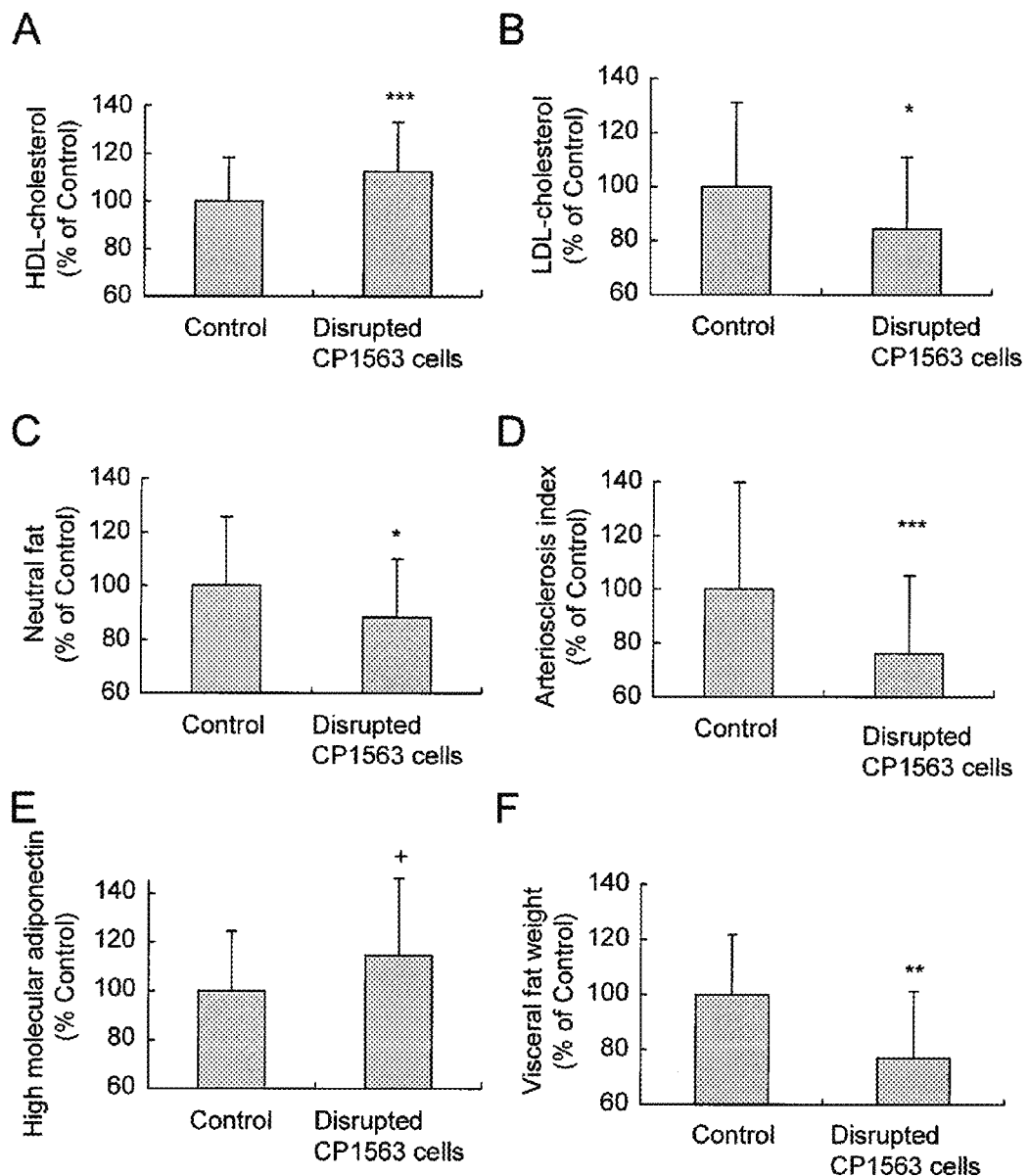
FIG. 6 is the graph showing an anti-metabolic-syndrome effect of disrupted cells of a lactic acid bacterium on a dietary-induced obesity model, wherein "A" shows HDL-cholesterol; "B" shows LDL-cholesterol; "C" shows neutral fat; "D" shows an arteriosclerosis index, "E" shows high molecular adiponectin; and "F" shows a visceral fat weight.

The results are shown in FIG. 6A to FIG. 6F. As shown in FIGS. 6 B, C, D, and F, the levels of LDL-cholesterol, neutral fat, arteriosclerosis index, and visceral fat weight were significantly lowered as a result of administration of disrupted cells of the strain CP1563. As shown in FIG. 6A and in FIG. 6E, the levels of HDL-cholesterol and polymeric adiponectin were significantly elevated as a result of administration of disrupted cells of the strain CP1563. Thus, the lipid metabolisms of the obesity mouse models was significantly improved by administration of the disrupted cells of the lactic acid bacterium.

EXAMPLE 5

In this Example, the lactic acid bacterium was compared with organic-solvent-extract of the same lactic acid bacterium.

The obesity mouse model described in Example 2 was raised by feeding various high-fat feeds (i.e., the group to which the control feed was administered, the group to which the feed containing 1% disrupted CP1563 was administered, and the group to which the feed containing 0.1% organic-solvent-extract of the strain CP1563 was administered). As described in Comparative Example, 1 g of the organic-solvent-extract can be obtained from 10 g of the bacterium. As such, 1% incorporation of the strain into the feed is equivalent to 0.1% incorporation of the organic-solvent-extract of the same strain. Thereafter, HDL-cholesterol levels in the mouse model of obesity were measured.

Figure 7:
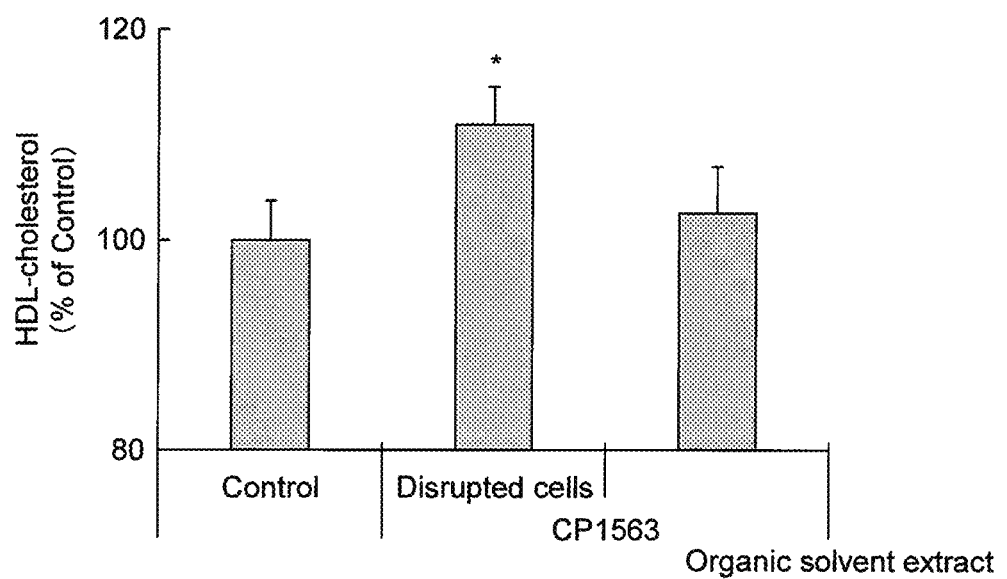
FIG. 7 is the graph showing an effect of disrupted cells of a lactic acid bacterium on a dietary-induced obesity model in comparison with the effect of an organic-solvent extract of the same lactic acid bacterium.

The results are shown in FIG. 7. As shown in this figure, no changes were observed in the HDL cholesterol level of the group to which the organic-solvent-extract of the strain CP1563 was administered; however, the HDL cholesterol level was significantly improved in the group to which disrupted cells of the strain CD1563 had been administered ($p=0.021$).

EXAMPLE 6

In this Example, the influence of degrees of cell breaking on the effect of a lactic acid bacterium on dietary-induced obesity mouse model was examined.

Specifically, the sterilized suspension of the *Lactobacillus amylovorus* strain CP 1563 described in Example 1 was subjected to disruption by three methods as described below.

Disruption 1: Disruption Using Dry-Type Jet Mill

The sterilized suspension of the lactic acid bacterium was lyophilized to obtain a powder, which was then subjected to disruption treatment in the manner as described below.

Apparatus used: dry-type jet-mill cell disruptor (Jet-O-Mizer)
    Feeding speed: 0.5 g/min
    Discharge pressure: 6 kg/cm$^2$
    Number of treatments: once Disruption 2: Disruption with Dyno-Mill (Wet-Type)

Treatment was carried out as described in Example 1.

Disruption 3: Disruption Using Dry-Type Satellite Mill

The sterilized suspension of the lactic acid bacterium was lyophilized to obtain a powder, which was then subjected to disruption treatment in the manner as described below.

Apparatus used: dry-type satellite mill cell disruptor (GOT5 Galaxy 5)
    Pot used: 500 cc×2
    Balls used: 32.3 g of 10-mm zirconia balls
    300 g of 5-mm zirconia balls
    250 g of 1-mm alumina balls
    Rounds of spinning: revolution: 240 rpm; rotation: 180 rpm
    Treatment time: 5 hours As a result of the breaking treatment as described above, the average long diameter of cells was 2.41 µm in the case of Disruption 1, 1.89 µm in the case of Disruption 2, and 0.45 µm in the case of Disruption 3, respectively, and these sizes were 87%, 68%, and 16% of the average long diameter in the case of no disruption treatment (2.77 µm), respectively.

The obesity mouse model described in Example 2 was raised by feeding various high-fat feeds (i.e., the group to which the control feed was administered (Disruption 1), the group to which the feed containing 1% disrupted CP1563 cells was administered (Disruption 2), and the group to which the feed containing 1% disrupted CP1563 cells were administered (Disruption 3)).

Figure 8:
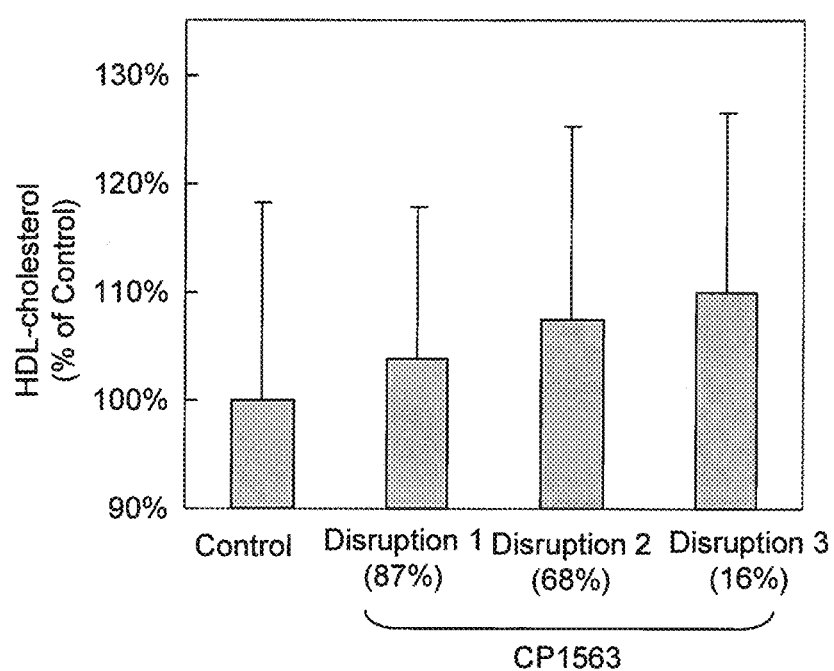
FIG. 8 is the graph showing an effect of disrupted cells of a lactic acid bacterium, which were prepared under different disruption conditions, on a dietary-induced obesity model (HDL-cholesterol).

The results are shown in FIG. 8. The results demonstrate that any broken bacterial cells could exert the effect of improving the lipid metabolism, regardless of methods of cell disruption. Further, it was found that the HDL cholesterol level was improved as the degree of cell breaking was elevated.

EXAMPLE 7

In this Example, the effect of a lactic acid bacterium on the dietary-induced obesity mouse model was examined.

The lactic acid bacterium *Lactobacillus amylovorus* CP1562 was sampled and isolated from human feces. This strain was identified based on 16S rDNA nucleotide sequence analysis and phenotype observation. The strain obtained herein was deposited under Accession Number: FERM BP-11379 as of Apr. 22, 2011, with the International Patent Organism Depositary, the National Institute of Advanced Industrial Science and Technology (AIST) (Tsukuba Central 6, 1-1-1 Higashi, Tsukuba, Ibaraki, 305-8566, Japan) under the terms of the Budapest Treaty for deposition of patent microorganisms.

The *Lactobacillus amylovorus* strain CP1562 prepared in the manner described above was subjected to disruption using a Dyno-Mill by the method described in Example 1. Disrupted cells were prepared, and the obesity mouse model described in Example 2 were raised by feeding various high-fat feeds (i.e., the group to which the control feed was administered, the group to which the feed containing 1% disrupted CP1563 cells was administered, and the group to which the feed containing 1% disrupted CP1562 cells was administered).

Figure 9:
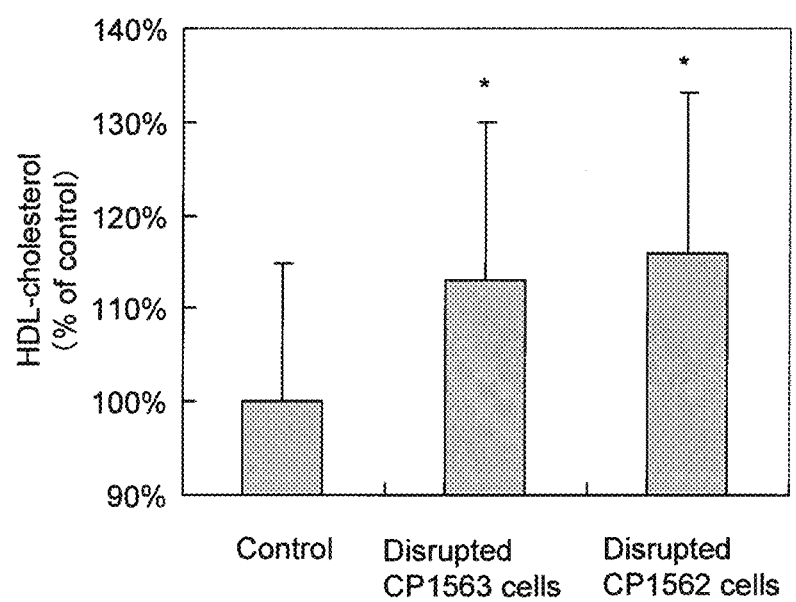
FIG. 9 is the graph showing an effect of disrupted cells of the lactic acid bacterium *Lactobacillus amylovorus* strain CP1562 on a dietary-induced obesity model (HDL-cholesterol).

The results are shown in FIG. 9. The results demonstrate that the HDL cholesterol level in the group to which the feed containing disrupted CP1562 cells was administered was significantly improved, compared with the control group.

EXAMPLE 8

Preparation of Variants

The *Lactobacillus amylovorus* strain CP1563 or CP1562 was subjected to static culture in MRS medium until it reached the logarithmic growth phase, and then washed with sterilized physiological saline or sterilized water, and the washed strain was treated with 50 to 500 µg/ml N-methyl-N'-nitro-N-nitrosoguanidine (NTG) in the sterilized physiological saline or sterilized water at 30° C. to 37° C. for 30 to 60 minutes to obtain variants. Mutagenesis can be induced with the use of ultraviolet rays, ethylmethane sulfonate (EMS), and an anti-cancer agent such as Fluorouracil (5-FU) in addition to NTG and a well-known means can be adopted. Whether or not the obtained strain is *Lactobacillus amylovorus* can be determined by inspecting: nucleotide sequence homology of the 16S rRNA gene; DNA-DNA homology via DNA-DNA hybridization with a reference strain; or sugar assimilability.

EXAMPLE 9

Cell Breaking with Cell Wall Lysing Enzyme

Cell breaking can be achieved using conventional lytic enzymes such as egg white lysozyme (Roche and others), Mutanolysin (Wako Pure Chemical Industries, Ltd.), Lysostaphin (Wako Pure Chemical Industries, Ltd.), Labiase (Seikagaku Corporation), chitinase, Snail Enzyme (Sigma), β-glucuronidase (Sigma), or N-acetylmuramidase (Wako Pure Chemical Industries, Ltd.). As food materials, food-additive-grade lytic enzymes are used. Use of egg white lysozyme (Eisai Food & Chemical Co., Ltd. and others), chitinase (Rakuto Kasei Industrial Co., Ltd.), chitosanase (HBI Enzymes Inc. and others), and the like is preferable.

Cell breaking is conducted by suspending cells in an amount of 1% to 10% in 0.1M phosphate buffer (pH 6 to 7) and adding an optimal amount (between 0.1% and 1%) of a lytic enzyme. After the cells are retained at 37° C. for 1 to 24 hours, the lysis conditions are confirmed using an ultra-deep shape measuring microscope (VK-8500, KEYENCE). The cells are sterilized at a temperature of 100° C. and aseptically lyophilized to obtain a powder of broken cells.

EXAMPLE 10

Cell Breaking with Use of Surfactant

Cell breaking can also be conducted using a surfactant as a food additive, such as glycerin fatty acid ester, soybean lecithin, or egg yolk lecithin. One (1) volume of 50% surfactant is added relative to ten (10) volumes of cell suspension, and the resultant is incubated at 20° C. for 3 days. The lysis conditions are confirmed using an ultra-deep shape measuring microscope (VK-8500, KEYENCE) over time, and a solution of more preferable disrupted cells can be obtained.

EXAMPLE 11

Cell Breaking via Autolysis Treatment

Lactic acid bacterium is cultured, collected, washed, and then collected by the method as described in Example 1. The collected bacterial cells are then suspended in deionized water at an amount of 1/10 to 1/20 of the culture scale. Alternatively, lactic acid bacterium is cultured, collected, washed, and then collected by the method as described in Example 1. The collected bacterial cells are then resuspended in an adequate amount of water, the resulting suspension is lyophilized without sterilization, and 1 kg of the obtained dry powder of lactic acid bacterium is then suspended in 20 L of deionized water. The obtained suspensions of lactic acid bacterium are allowed to stand at 50° C. for 1 to 3 days for autolysis. The autolysis product is sterilized by the method as described in Example 1 and lyophilized to obtain a lyophilized powder of the autolytic lactic acid bacterium. The product is continuously observed using an ultra-deep shape measuring microscope (VK-8500, KEYENCE).

All publications, patents, and patent applications cited herein are incorporated herein by reference in their entirety.

Industrial Applicability

The present invention provides an agent for improving the lipid metabolism and the use thereof. Since the agent for improving the lipid metabolism of the present invention is capable of normalizing the lipid metabolism, such agent can be used for prevention or treatment of various types of diseases or disorders. Accordingly, the present invention is useful in the fields of, for example, medicaments, foods or drinks, and animal husbandry.

Accession Numbers:

FERM BP-11255: *Lactobacillus amylovorus* strain CP1563, deposited as of May 25, 2010

FERM BP-11256: *Lactobacillus gasseri* strain CP3238, deposited as of May 25, 2010

FERM BP-11379: *Lactobacillus amylovorus* strain CP1562, deposited as of Apr. 22, 2011

The invention claimed is:

1. A method for enhancing an effect of a lactic acid bacterium on lipid metabolism in a subject, comprising:
   (a) breaking the lactic acid bacterium to produce a composition consisting essentially of as the active ingredient broken cells of the lactic acid bacterium by grinding, milling, enzyme treatment, chemical treatment or lysis, such that the long diameter of a broken cell of the lactic acid bacterium is 90% or less of the long diameter of the lactic acid bacterium before breaking; (b) orally administering the composition to a vertebrate animal subject; and (c) enhancing lipid metabolism in the subject.

2. The method according to claim 1, wherein the broken cells of lactic acid bacterium are obtained via physical disruption, chemical treatment, or lysis.

3. The method according to claim 1, wherein the lactic acid bacterium is at least one or at least two bacteria selected from the group consisting of *Lactobacillus amylovorus* strain CP1563, *Lactobacillus amylovorus* strain CP1562, and *Lactobacillus gasseri* strain CP3238.

4. The method according to claim 1, wherein the lactic acid bacterium is broken such that the long diameter of a broken cell of the bacterium is 70% or less of that of before breaking.

5. The method according to claim 1, wherein the vertebrate animal subject is at risk of having a lipid metabolism-associated disease or disorder.

6. The method according to claim 5, wherein the lipid metabolism-associated disease or disorder is arteriosclerosis, hyperlipidemia, fatty liver, diabetes, myocardial infarct, or cerebral infarction.

7. The method according to claim 1, wherein the composition comprising broken cells of the lactic acid bacterium is formulated into a powder, granules, tablet, capsule or a liquid formulation prior to administering the composition to the mammal.

8. The method of claim 1, wherein the composition comprising broken cells of the lactic acid bacterium is formulated into a food or a drink prior to administering the composition to the mammal.

9. The method of claim 1, wherein the vertebrate animal subject is a human.

10. The method of claim 1, wherein the lactic acid bacterium is *Lactobacillus* or *Bifidobacterium*.

11. The method of claim 1, wherein the lactic acid bacterium is *Lactobacillus amylovorus* or *Lactobacillus gasseri*.

12. A method for enhancing an effect of a lactic acid bacterium on lipid metabolism in a subject, comprising:
   (a) breaking the lactic acid bacterium by grinding, milling, enzyme treatment, chemical treatment or lysis, such that the diameter of a broken cell of the lactic acid bacterium is 2.5 µm or less of the diameter of the lactic acid bacterium before breaking, to produce a composition consisting essentially of as the active ingredient broken cells of the lactic acid,
   (b) orally administering the composition to a vertebrate animal subject; and
   (c) enhancing lipid metabolism in the subject.

13. The method of claim 12, wherein the diameter of a broken cell of the bacterium is 2 µm or less.

14. A method for enhancing an effect of a lactic acid bacterium on lipid metabolism in a subject, comprising:
   (a) breaking the lactic acid bacterium by grinding, milling, enzyme treatment, chemical treatment or lysis, such that the long diameter of a broken cell of the lactic acid bacterium is 90% or less of the long diameter of the lactic acid bacterium before breaking, to produce a composition consisting essentially of as the active ingredient broken cells of the lactic acid bacterium, and wherein the composition consisting essentially of as the active ingredient broken cells of the lactic acid bacterium is more effective than intact lactic acid bacterium at: (i) lowering at least one selected from the group consisting of the levels of total cholesterol, LDL-cholesterol, neutral fat, arteriosclerosis index, and visceral fat, or (ii) elevating a level of at least one of HDL-cholesterol and adiponectin, when administered to a mammal;
   (b) orally administering the composition to a vertebrate animal subject; and
   (c) enhancing lipid metabolism in the subject.

15. A method for enhancing an effect of a lactic acid bacterium on lipid metabolism in a subject, comprising:
   (a) breaking the lactic acid bacterium by grinding, milling, enzyme treatment, chemical treatment or lysis, such that the long diameter of a broken cell of the lactic acid bacterium is 90% or less of the long diameter of the lactic acid bacterium before breaking, to produce a composition consisting essentially of as the active ingredient broken cells of the lactic acid bacterium, wherein the composition consisting essentially of as the active ingredient broken cells of the lactic acid bacterium is more effective than intact lactic acid bacterium for treating a lipid metabolism-associated disease or disorder in a mammal;

(b) orally administering the composition to a vertebrate animal subject; and (c) enhancing lipid metabolism in the subject.

16. A method for enhancing an effect of a lactic acid bacterium on lipid metabolism in a subject, comprising:

(a) breaking the lactic acid bacterium to produce a composition comprising broken cells of the lactic acid bacterium, wherein the lactic acid bacterium is broken such that the average long diameter of a broken cell of the bacterium is 0% to 90% of the diameter of the lactic acid bacterium before breaking, and wherein the composition comprising broken cells of the lactic acid bacterium is more effective than intact lactic acid bacterium for treating arteriosclerosis, hyperlipidemia, fatty liver, diabetes, myocardial infarct, or cerebral infarction in a mammal; and (b) orally administering the composition to a vertebrate animal subject, wherein the effect of the lactic acid bacterium on lipid metabolism in the subject is enhanced compared to a composition comprising cells of a lactic acid bacterium that are not broken.

17. A method for enhancing an effect of a lactic acid bacterium on lipid metabolism in a subject, comprising:

orally administering to a subject a composition consisting essentially of as the active ingredient broken cells of the lactic acid bacterium, wherein the lactic acid bacterium was broken by grinding, milling, enzyme treatment, chemical treatment or lysis, such that the long diameter of a broken cell of the lactic acid bacterium is 90% or less of the long diameter of the lactic acid bacterium before breaking.

18. A method for enhancing an effect of a lactic acid bacterium on lipid metabolism in a subject, comprising:

orally administering to a subject a composition consisting essentially of as the active ingredient broken cells of the lactic acid bacterium, wherein the lactic acid bacterium was broken by grinding, milling, enzyme treatment, chemical treatment or lysis, such that the diameter of a broken cell of the lactic acid bacterium is 2.5 µm or less of the diameter of the lactic acid bacterium before breaking.

* * * * *